United States Patent [19]

Freeman

[11] Patent Number: 4,955,896
[45] Date of Patent: Sep. 11, 1990

[54] UNIVERSAL MEDICAL FORCEP TOOL
[76] Inventor: Jerre M. Freeman, 1509 Peabody, Memphis, Tenn. 38104
[21] Appl. No.: 780,808
[22] Filed: Sep. 27, 1985
[51] Int. Cl.⁵ ............................................. A61B 17/28
[52] U.S. Cl. ..................................... 606/210; 606/207
[58] Field of Search ............... 128/354, 321, 322, 346; 294/99.2; 606/210, 131, 133, 207, 211

[56] References Cited

U.S. PATENT DOCUMENTS

| | | | |
|---|---|---|---|
| 1,108,737 | 8/1914 | Gaudos | 128/340 |
| 3,503,398 | 3/1970 | Fogarty et al. | 128/322 |
| 4,457,756 | 7/1984 | Kern et al. | 128/325 X |

FOREIGN PATENT DOCUMENTS

| | | | |
|---|---|---|---|
| 214727 | 2/1924 | Fed. Rep. of Germany | 128/321 |
| 401732 | 9/1909 | France | 128/321 |

Primary Examiner—Michael H. Thaler
Attorney, Agent, or Firm—Bradford E. Kile

[57] ABSTRACT

This invention relates to a universal medical forcep tool having a main body portion for receiving a replaceable grasping portion having grasping tips and respective support handles on which the tips are mounted. The main body portion forms a receptacle for receiving the replaceable grasping portions.

11 Claims, 1 Drawing Sheet

U.S. Patent   Sep. 11, 1990   4,955,896
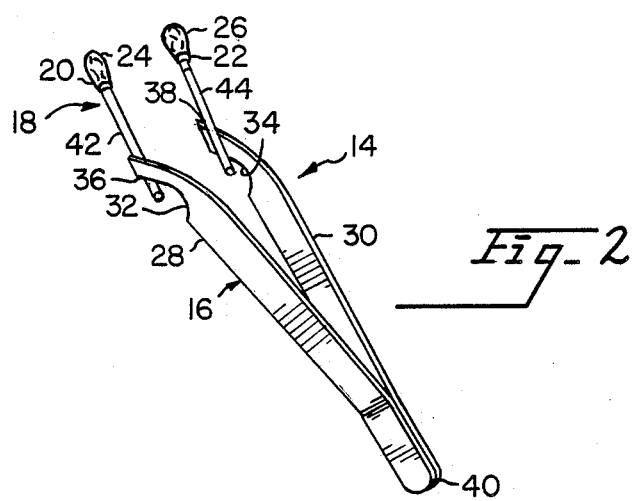
Fig_2
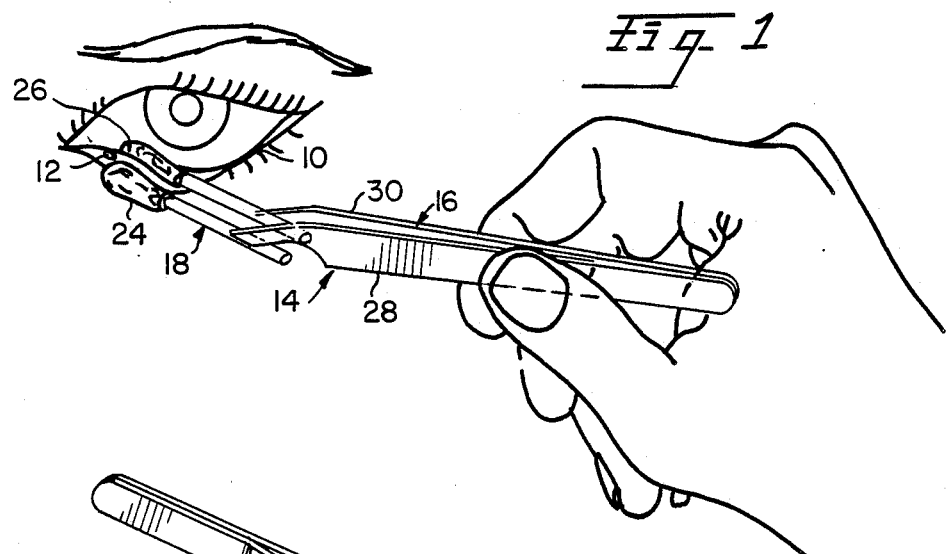
Fig_1
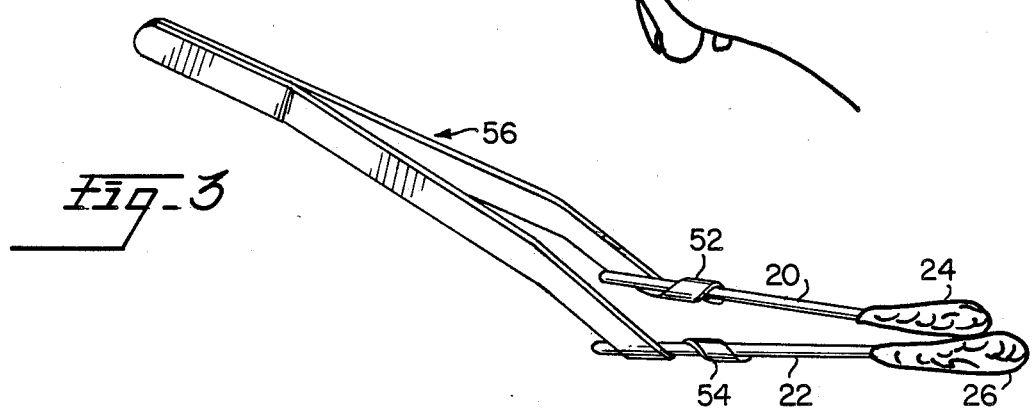
Fig_3
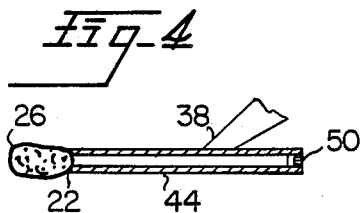
Fig_4
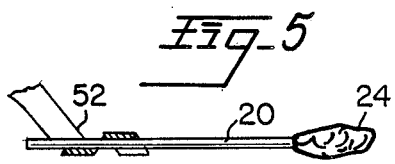
Fig_5

UNIVERSAL MEDICAL FORCEP TOOL

BACKGROUND OF INVENTION

This invention relates to a medical forcep tool. More particularly the present invention relates to a universal, medical forcep tool wherein a plurality of designs directed either to grasping tips or to handle configurations facilely provide an opportunity to perform a range of medical proceedings heretofore requiring a considerable library of instruments.

While the subject invention is envisioned as having application in variant medical environments, one context which is of particular interest pertains to medical forceps for gently but firmly grasping an eye lid during treatment of keratitis sicca or keratoconjunctivitis sicca.

Keratitis sicca or keratoconjunctivitis sicca (in layman's terms dry eye) is the result of insufficient production or excessive drainage of lacrimal fluid. Keratitis sicca is a frequently-encountered problem, especially in elderly patients. Conventional prior art practice in treating this condition has been to utilize various types of topical drops and ointments with varying degrees of success. Humidifiers or vaporizers have also been used and are often of great help in decreasing evaporation from the eye, but do nothing to limit the drainage of the lacrimal fluid. In this connection, applicant has invented a punctum plug for reversible occlusion of the punctum and canaliulus. For a more complete disclosure of the punctum plug invention reference may be had to applicant's prior U.S. Pat. No. 3,949,750, the disclosure of which is hereby incorporated by reference as though set forth at length.

During the foregoing procedure, a grasping pad is generally necessary for contacting an eye lid and holding the lid in a distended posture to expose a patient's punctum and canaliculus.

Although conventional forceps can be used to expose the punctal opening, metallic tipped instruments tend to be harsh and can easily irritate eye tissue. In addition, conventional forceps once used, must be resterilized which is time consuming and/or requires an extensive library of instruments. Accordingly it would be highly desirable to provide a physician with a forcep tool having soft pliable tips which would not irritate delicate eye tissue. Additionally it would be helpful to have a forcep that did not require resterilization after each use.

In addition to eye care, other procedures in the medical field exist wherein known forcep structures are not completely suitable for their intended purpose such as in plastic surgery procedures, treatment of burn victims, neurosurgery, etc. and other instances where it is necessary to gently handle tissue with a sterile grasping instrument.

For use in connection with the above and other medical procedures, a forcep user may desire to remove and replace a particular grasping portion for any one of many different reasons. For instance, a used grasping portion may need to be cleaned and/or sterilized. A forcep user may also desire a grasping portion of different characteristics, such as thin material, tip shape, size, configuration, etc.

In medical forcep type tools of the prior art each different set of grasping characteristics is typically embodied in a separate instrument. Each tool permanently embodies the characteristics of its one fixed grasping portion including grasping tips and respective supporting handles on which the tips are set. In essence, the grasping portion is of an integral construction with a main forcep body.

Often times, a medical forcep is used in a patient's internal cavities for grasping sensitive tissues or human organs. A physician must be very careful in narrowly restricted space between body tissues. Under such circumstances, an elongated support handle of varying configuration is desirable for operation. A different handle more suitable for a particular maneuver may be mounted to replace a handle of less accommodating configuration.

A medical forcep also needs to be sanitary. At times more than the grasping tip is contaminated during an operation and would require cleaning or replacement. A forcep with removable grasping tips does not provide for removal of supporting arms on which said tips are mounted. While such handles are cleaned, the entire forcep tool is temporarily made unavailable for use.

Removing a grasping tip from a medical forcep may also be an unpleasant task. Direct contact with the grasping tip is required and would contaminate a contacting hand as well as causing seepage of fluid or other tissues from the grasping tip. The contacting hand would need to be cleaned before mounting the forcep with a different tip.

The problems or difficulties suggested in the proceeding are not intended to be exhaustive, but rather are among many which may tend to reduce the effectiveness of prior medical forceps. Other noteworthy problems may also exist; however, those presented above should be sufficient to demonstrate that previously known forceps, for use in the medical field, will admit to worthwhile improvement.

OBJECTS OF THE INVENTION

It is a general object of the invention to provide a universal medical, forcep tool which will obviate or minimize problems and disadvantages of the type previously described.

It is another object of the invention to eliminate the need for constructing entirely separate medical forcep tools for accommodating different sets of user requirements of designs and conditions of the grasping section including grasping tips and respective arm portions on which the tips are mounted.

It is a particular object of the invention to proved a novel medical forcep having a replaceable grasping section including grasping tips and respective supporting handles on which the tips are mounted, for expedient disposal or sterilization apart from the main body of the forcep, or for expedient exchange to a grasping section of different design.

It is a further object of the invention to provide a receptacle forming a main forcep body portion for receiving replaceable grasping structures.

It is yet a further object of the invention to provide a novel medical forcep having grasping tips made of material not prone to shed surface matter during use.

It is another object of the invention to provide a universal medical forcep tool in accordance to any combination of the foregoing objects.

BRIEF SUMMARY

A universal medical forcep tool which is intended to accomplish at least some of the foregoing objects includes an instrument having a main body portion and a grasping portion. The main body portion is suitable for releasably receiving a disposable or replaceable grasping portion. The grasping portion includes elongated members of selected configuration on which are mounted grasping tips.

One Preferred Embodiment

One preferred embodiment of the instant invention includes a forcep having a main body portion including two cylindrical hollow tubes for slidability receiving two elongate handled swabs with soft grasping tips in a frictionally engaged relationship. The cylindrical tubes are in turn attached to respective arms of a forcep body which is self biased to a normally open position.

Another Preferred Embodiment

Another preferred embodiment of the instant invention includes a forcep having a main body portion including two tubular spiral formations for slidably receiving swabs in frictional engagement. The tubular spiral formations have angled end portions on respective arms of the forcep main body which are biased in an open posture.

BRIEF DESCRIPTION OF DRAWINGS

FIG. 1 is an axonometric view of a universal medical forcep according to one preferred embodiment of the subject invention positioned in an operative posture adjacent a patient's eye;

FIG. 2 is another axonometric view of a forcep in accordance to a preferred embodiment of the instant invention, as shown generally in FIG. 1;

FIG. 3 shows a forcep in accordance to another preferred embodiment of the instant invention;

FIG. 4 is a partially cross-section, detail view of a receptacle constituting a main body portion of the forcep disclosed in FIG. 2 for receiving a replaceable grasping section; and FIG. 5 is a partially cross-section, detail view of a receptacle constituting a main body portion of the forcep of FIG. 3 for receiving a facilely replaceable, grasping section.

DETAILED DESCRIPTION

Referring now to the drawings wherein like numerals indicate like parts, there will be seen various views of preferred embodiments in accordance with the instant invention.

Context of the Invention

Prior to presenting a detailed discussion of specific embodiments, a few brief comments with respect to the operative context of the invention may be worthwhile. In this connection and with reference to FIG. 1 there will be seen one environment in which a physician may advantageously utilize the instant invention. More specifically, and as previously noted in applicant's prior U.S. Pat. No. 3,949,750, one advantageous procedure to treat keratitis sicca is to provide a reversible occlusion of the punctum and canaliculus. In order to insert a punctum plug as described in my prior patent, and as shown in FIG. 1, it is necessary to gently grasp a patient's lower eye lid 10 to expose a punctal opening 12. In order to achieve this grasping function, a universal medical forcep instrument 14, which will be described in detail below, is depicted in the hand of a physician.

Universal Medical Forcep Tool

FIGS. 1-2 illustrate one preferred embodiment of the instant invention. These Figures show a forcep 14 including a first main body portion 16 and a second replaceable grasping section 18.

The replaceable grasping section 18 includes elongated support handles 20 and 22 which are slidably received in frictional engagement within portions of the forcep main body 16. The elongate support handles 20 and 22 terminate with pliable, resilient tips 24 and 26 respectively which are exposed for grasping functions. The elongated support handles are not readily seen in FIG. 1 because they are slidably received within the forcep body as will be discussed below.

The main body portion 16 includes first and second arms 28 and 30, each having bent intermediate portions 32 and 34 and end portions 36 and 38. The arms 28 and 30 are joined at one end 40 and are self biased away from each other in a manner known in the forcep art.

The main forcep body portion 16 also includes two cylindrical hollow tubes 42 and 44 which are joined to the end structures 36 and 38 at an obtuse angle. The forcep main body portion 16 serves as a receptacle for receiving in its end structure a replaceable grasping section for forming a complete medical forcep tool.

As detailed in FIG. 4, the cylindrical hollow tube 44 operably receives in frictional engagement a support handle 22 of a grasping member. Sterile swabs may be easily removed and new swabs inserted into the hollow cylindrical tubes as desired.

It should be noted that in one embodiment the cylindrical hollow tubes 42 and 44 may include a cap 50 at an end opposite to the grasping tips of the swabs as shown in FIG. 4. Alternatively the ends of the tubes may remain open to facilitate changing of swabs.

As shown in FIG. 1, a physician applies pressure on arms 28 and 30 against the self bias of the arms to induce grasping tips 24 and 26 of swabs to travel toward each other for grasping an eye lid in an ophthalmic procedure. Since the support handles of the swabs are slidably received in frictional engagement within the cylindrical hollow tubes 42 and 44, movement of the forcep arms 28 and 30 by a user are translated to the swabs via the angularly placed cylindrical tubes.

The tips of the grasping members 18 are composed of a soft pliable material such as sponge rubber, cotton, silicon, etc. to delicately handle body tissue. Moreover the shape of the tips 24 and 26 may be advantageously configured to facilitate grasping.

FIG. 3 illustrates a second preferred embodiment of the instant invention. The only difference from the first embodiment described above is that the cylindrical hollow tubes 42 and 44 are replaced by tubular spiral formations 52 and 54. The tubular spiral formations comprise the end structure receiving the swab handles 20 and 22 in a guiding frictional relationship, and wraps around at least a portion of said handles. The swab handles are slidably received within the spirals as shown. The forcep main body portion 56 includes the tubular spiral formation end structure, and constitutes a receptacle for receiving a replaceable grasping section (swabs) to form a complete forcep tool.

FIG. 5 illustrates a partial sectional view of spiral formation 52 receiving handle 20 of swab 24. The other spiral formation 54 is of similar construction in relation to swab 26. Together, the swabs 24 and 26 constitute a replaceable grasping section slidably received in spiral formations 52 and 54 of the forcep main body portion. Although the handles 20 and 22 of the grasping sections are shown as being straight, in the embodiment depicted in FIGS. 3 and 5 these sections may be accurate or angled in three dimensions to accommodate a variety of uses.

While the instant invention is described above in the context of only two specific embodiments, other configurations and/or conditions may be envisioned by one skilled in the art. For instance, the replaceable portions need not be cotton tipped members. The tips may be composed of other kinds of grasping sections having grasping tips and support handles on which the tips are mounted as previously described. Further, the swab tip need not be composed of cotton material; soft silicon based material or other medically compatible material may be suitable for the subject medical forcep. Moreover the outer surface of the tip may be frictional to facilitate engagement with body tissue.

Any one of many attachment relationships between the forcep body portion and the replaceable grasping portion may be suitable; the main requirement being that user manipulation of the forcep arms is translated to the detachable grasping sections. The attachment need not be entirely frictional. An affirmative coupling assembly such as a screw thread may be employed. Furthermore, the instant invention is not limited to the specific forcep arm structure disclosed in the preferred embodiments. One skilled in the art is aware that many different forcep arm structures are available and may be adaptable for practicing the instant disclosed invention, and that many different end structures may be used for receiving the replaceable grasping section.

Summary of Major Advantages of the Invention

In describing a universal medical forcep tool in accordance with a preferred embodiment of the invention those skilled in the art will recognize several advantages, which singularly distinguish the subject invention from the heretofore known prior art.

A particular advantage of the subject invention is the provision of replaceable grasping portions including grasping tips and supporting handles on which the tips are mounted. In this manner, supporting handles of varying configuration may be easily interchanged to accommodate the conditions of a particular task.

Another advantage of the subject invention is the provision to enable removal of a grasping tip without directly contacting said grasping tip. In this manner, a physician's hand won't be contaminated, and materials in or on a grasping tip may be better contained.

Another advantage of the subject invention is the provision to enable more than the grasping tips of a medical forcep to be removed for disposal or sterilization. It promotes better assurance of a clean and sterilized medical forcep tool.

These stated advantages are by no means exhaustive and more will be evident to one with ordinary skill in the art after reading the above disclosure.

In describing the invention, reference has been made to preferred embodiments for illustrating the instant invention. Those skilled in the art, however, familiar with the instant disclosure of the subject invention, may recognize additions, deletions, modifications, substitutions, and/or other changes which may fall within the purview of the subject claims.

I claim:

1. A universal medical forcep tool comprising:
   a main body portion,
      said main body portion having first and second arms joined at a first end and operably extend in variable relative position responsive to external control;
   a first replaceable grasping section connected to said first arm and having,
      a first support handle, and
      a first resilient grasping tip mounted on a distal end of said first support handle;
   a second replaceable grasping section connected to said second arm and having,
      a second support handle, and
      a second resilient grasping tip mounted on a distal end of said second support handle;
   said first replaceable grasping section operably working in cooperation with said second replaceable grasping section for gently engaging material between said first and second replaceable grasping tips;
   each said first and second arms includes an end structure remote from said first end for removably receiving said first and second support handle respectively and for operably holding said first and second resilient grasping tips in a mutually opposing posture; and
   said first and second resilient grasping tips operably move toward each other for gentle engagement of material between said grasping tips responsive to external manipulation of said first and second arms.

2. A universal medical, forcep tool as defined in claim 1 wherein:
   each of said end structures comprises a cylindrical hollow tube; and
   each cylindrical hollow tube being in frictional engagement with a support handle slidably received therein.

3. A universal medical forcep tool as defined in claim 1 wherein:
   each of said end structures comprises a tubular spiral formation; and
   each tubular spiral formation being in frictional engagement with a support handle slidably received therein.

4. A universal medical forcep tool according to claim 1 or 2 wherein:
   said first and second resilient grasping tips are composed of cotton material.

5. A universal medical forcep tool according to claim 1, 2, or 3 wherein:
   said first and second resilient grasping tips are composed of silicon based material.

6. A universal medical forcep tool as defined in claim 1, 2, or 3 wherein:
   said grasping tip is pliable and suitable for use in safely grasping tissues of a human body.

7. A universal medical tool as defined in claim 1, 2, or 3 wherein:
   each said first and second support handle comprises a generally elongated rod.

8. A universal medical forcep tool as defined in claim 1, 2, or 3 wherein:
   each said first and second end structures is angularly positioned with an obtuse angle in relation to remaining portions of a corresponding arm extension.

9. A universal medical forcep tool, as defined in claim 8 wherein:

each of said first and second support handles is a generally elongated rod.

10. A universal medical forcep tool as defined in claim 2, wherein:
   each of said cylindrical hollow tubes is open at both ends thereof.

11. A universal medical forcep tool comprising:
   a main body portion,
      said main body portion having first and second arms joined at a first end and operably extend in variable relative position responsive to external control;
   a first replaceable grasping section connected to said first arm and having,
      a first support handle, and
      a first resilient grasping tip mounted on a distal end of said first support handle;
   a second replaceable grasping section connected to said second arm and having,
      a second support handle, and
      a second resilient grasping tip mounted on a distal end of said second support handle;
   said first replaceable grasping section operably working in cooperation with said second replaceable grasping section for gently engaging material between said first and second replaceable grasping tips;
   each said first and second arms includes an end structure comprising a tubular spiral formation remote from said first end, each tubular spiral formation being in frictional engagement with a support handle slidably received therein, for removably receiving said first and second support handles respectively, and operably holding said first and second resilient grasping tips in a mutually opposing posture; and
   each of said first and second resilient grasping tips being composed of cotton material and each of said grasping tips operably move toward each other for gentle engagement of material between said grasping tips responsive to external manipulation of said first and second arms.

* * * * *